(12) United States Patent
Ghabra et al.

(10) Patent No.: US 10,363,129 B2
(45) Date of Patent: Jul. 30, 2019

(54) VARIABLE STRENGTH INTRAOCULAR LENS AND METHOD OF USING SAME

(71) Applicant: MAG OPTICS LTD., London (GB)

(72) Inventors: Marwan Ghabra, London (GB); Hakam Ghabra, London (GB)

(73) Assignee: Mag Optics, London (GB)

( * ) Notice: Subject to any disclaimer, the term of this patent is extended or adjusted under 35 U.S.C. 154(b) by 23 days.

(21) Appl. No.: 15/651,670

(22) Filed: Jul. 17, 2017

(65) Prior Publication Data

US 2017/0312071 A1 Nov. 2, 2017

Related U.S. Application Data

(63) Continuation of application No. PCT/IB2016/000105, filed on Jan. 19, 2016.

(60) Provisional application No. 62/104,119, filed on Jan. 16, 2015.

(51) Int. Cl.
*A61F 2/16* (2006.01)
*A61F 2/14* (2006.01)

(52) U.S. Cl.
CPC .......... *A61F 2/1629* (2013.01); *A61F 2/1648* (2013.01); *A61F 2/1651* (2015.04); *A61F 2/15* (2015.04); *A61F 2002/1681* (2013.01); *A61F 2002/1682* (2015.04); *A61F 2002/1689* (2013.01); *A61F 2002/169053* (2015.04); *A61F 2220/0075* (2013.01); *A61F 2250/0007* (2013.01)

(58) Field of Classification Search
CPC .... A61F 2/1629; A61F 2/1651; A61F 2/1648; A61F 2/15; A61F 2002/169053; A61F 2002/1681; A61F 2002/1689; A61F 2002/169; A61F 2220/0075; A61F 2250/0007

See application file for complete search history.

(56) References Cited

U.S. PATENT DOCUMENTS

| 8,834,566 B1 * | 9/2014 | Jones | A61F 2/1624 |
| | | | 623/6.22 |
| 2014/0371851 A1 | 12/2014 | Aharoni | A61F 2/16 |

FOREIGN PATENT DOCUMENTS

| WO | WO 02/071983 | 9/2002 | ............ A61F 2/16 |
| WO | WO 06/103674 | 10/2006 | ............ A61F 2/16 |
| WO | WO 12/023133 | 2/2012 | ............ A61F 2/16 |

OTHER PUBLICATIONS

International Search Report and Written Opinion for PCT Patent Application No. PCT/IB2016/000105 dated Jun. 13, 2016.
International Preliminary Report on Patentability, PCT Application No. PCT/IB2016/000105 dated Jul. 18, 2017.

* cited by examiner

*Primary Examiner* — David H Willse
*Assistant Examiner* — Tiffany P Shipmon
(74) *Attorney, Agent, or Firm* — J. Peter Paredes; David G. Rosenbaum; Rosenbaum IP, P.C.

(57) ABSTRACT

The present disclosure provides intraocular artificial lenses having a variable optical strength and methods of treating an eye disorder, such as presbyopia, using same. In some embodiments, the intraocular artificial lens comprises two optical elements that are moveable along the optical axis in relation to each other, for example in response to the accommodative process of the eye.

10 Claims, 22 Drawing Sheets

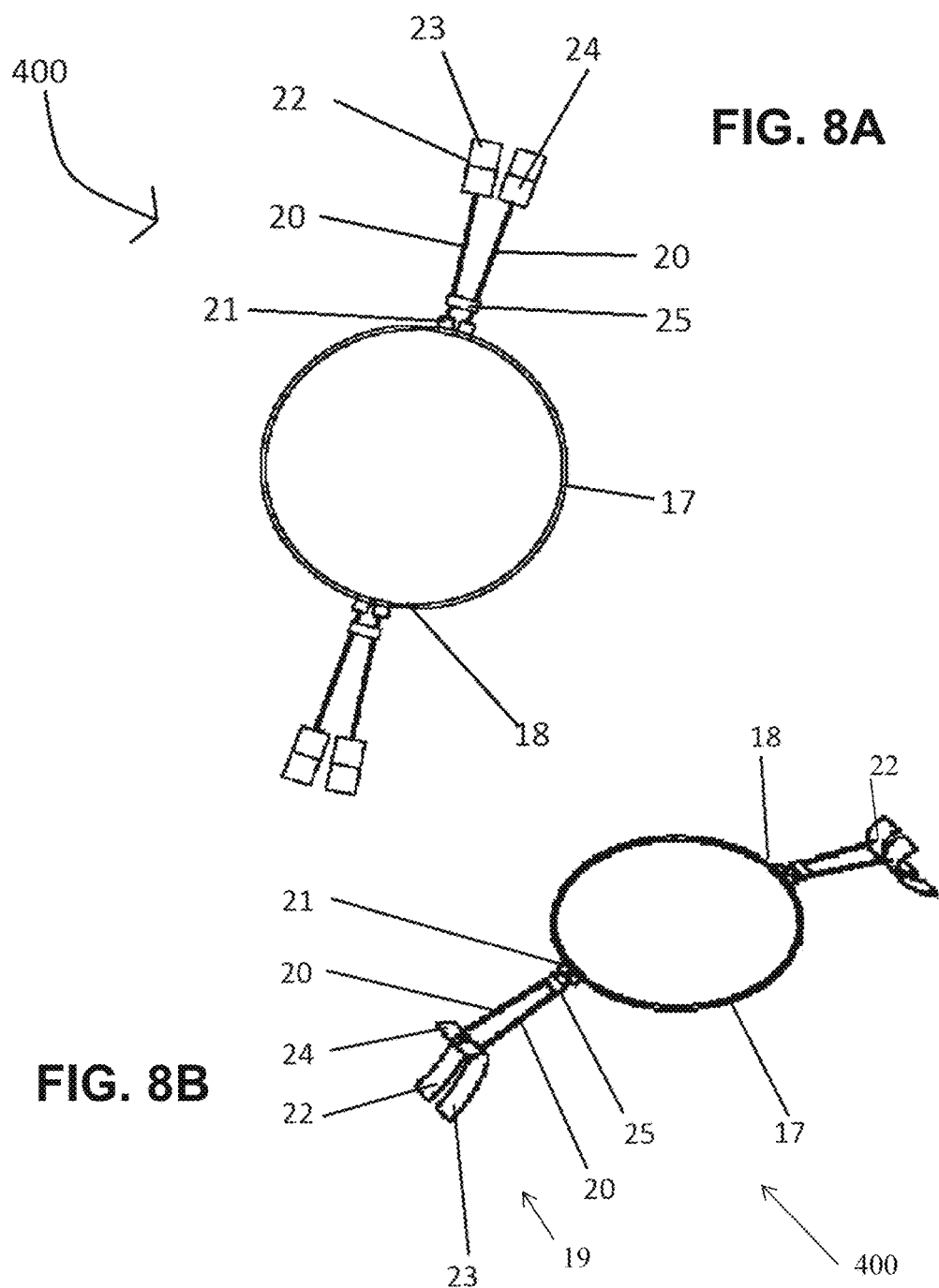

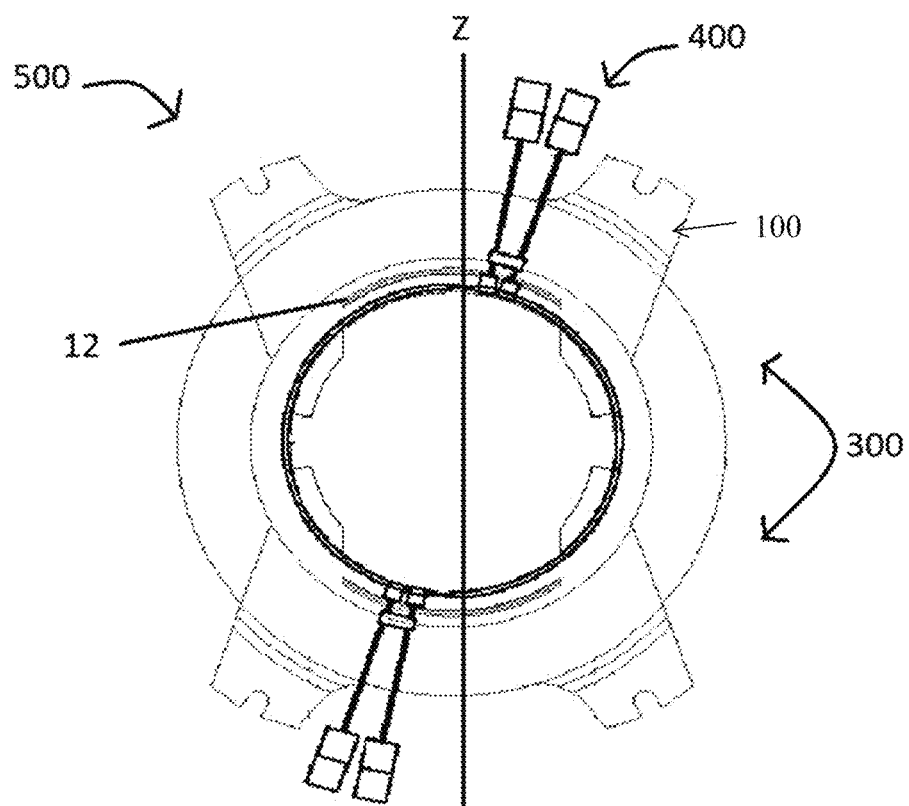
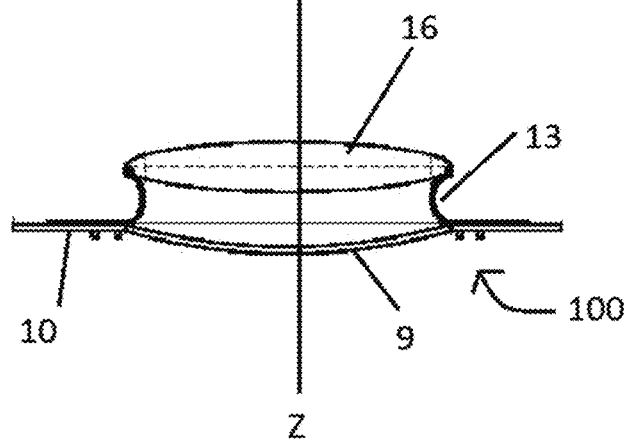
FIG. 14

VARIABLE STRENGTH INTRAOCULAR LENS AND METHOD OF USING SAME

CROSS REFERENCE TO RELATED APPLICATIONS

The present application claims priority to, and is a continuation application from, PCT Application Serial No. PCT/IB2016/000105, filed Jan. 19, 2016, which claims priority from U.S. Provisional Application Ser. No. 62/104,119, filed Jan. 16, 2015, all of which are incorporated hereto by reference in their entireties.

TECHNICAL FIELD

The present disclosure relates to intraocular artificial lenses having a variable optical strength and methods of treating an eye disorder, such as presbyopia, using same.

BACKGROUND

The vast majority of cataract operations involve the implantation of artificial intraocular lenses following the removal of the cataract. Typically, the implanted lenses have a fixed focal length and therefore a fixed power. Sometimes, the implanted lenses are bifocal or multi-focal, but each of the focal lengths of such lenses are still fixed.

After placement of such lenses, the accommodative process of the eye is no longer able to provide variable optical strength. There is a need for an intraocular lens responsive to the accommodative process of the eye.

SUMMARY

The present disclosure provides intraocular artificial lenses having a variable optical strength. In some embodiments, the artificial lens comprises at least two optical elements, at least two of which are moveable along the optical axis in relation to each other. The variable optical strength of the lens complex is a function of the relative position of at least two the optical elements to each other along the optical axis. The optical strength is varied by converting the compressive force of the ciliary muscle to increase the distance between the at least two optical elements.

In one embodiment, the present disclosure provides a variable optical strength intraocular lens comprising a lens complex comprising an anterior segment comprising an anterior lens, a posterior segment comprising a concave lens portion and a haptic plate portion, wherein the haptic plate portion substantially surrounds an optical zone, and at least one spring in contact with the anterior segment and the posterior segment to provide a separation distance between the anterior lens and the concave lens; and a ciliary haptic complex comprising a central ring, a first ciliary muscle haptic pair extending outwardly from the central ring, and a second ciliary muscle haptic extending outwardly from the central ring, wherein upon insertion into an eye, the central ring is in contact with an inferior side of the anterior lens and the first and second ciliary muscle haptic pairs are in communication with ciliary muscle of the eye.

In another embodiment, the present disclosure provides a method of treating a subject having an eye disorder, the method comprising removing a lens from the eye; inserting a lens complex into the eye, the lens complex comprising an anterior segment comprising an anterior lens, a posterior segment comprising a concave lens portion and a haptic plate portion, wherein the haptic plate portion substantially surrounds an optical zone, and at least one spring in contact with the anterior segment and the posterior segment to provide a separation distance between the anterior lens and the concave lens; inserting a ciliary haptic complex into the eye, the ciliary haptic complex comprising: a central ring, a first ciliary muscle haptic extending outwardly from the central ring, and a second ciliary muscle haptic extending outwardly from the central ring; contacting ciliary muscle of the eye with the first ciliary muscle haptic and with the second ciliary muscle haptic; positioning the central ring against an inferior side of the anterior lens to form a variable optical strength intraocular lens; and calibrating the variable optical strength intraocular lens.

These and other embodiments are described in greater detail below with reference to the figures.

BRIEF DESCRIPTION OF THE DRAWINGS

FIG. 8A shows a perspective view of a ciliary haptic complex according to one embodiment of the present disclosure from a superior position.

FIG. 8B shows a perspective view of the ciliary haptic complex of FIG. 8A.

FIG. 14 shows anterior posterior and cross sectional views of a coupled lens complex and ciliary haptic complex according to one embodiment of the present disclosure.

DETAILED DESCRIPTION

The present disclosure provides intraocular lenses ("IOLs") having a variable optical strength and methods of treating a subject using same. In particular, subjects having eyesight defects, such as presbyopia or a cataract, may benefit greatly from treatment comprising replacing a lens of the subject's eye with an IOL consistent with the present disclosure.

Figure 1:
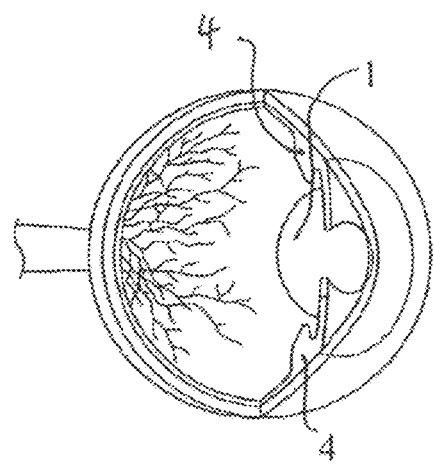
FIG. 1 shows an anterior to posterior cross sectional view of a human eye.
Figure 2:
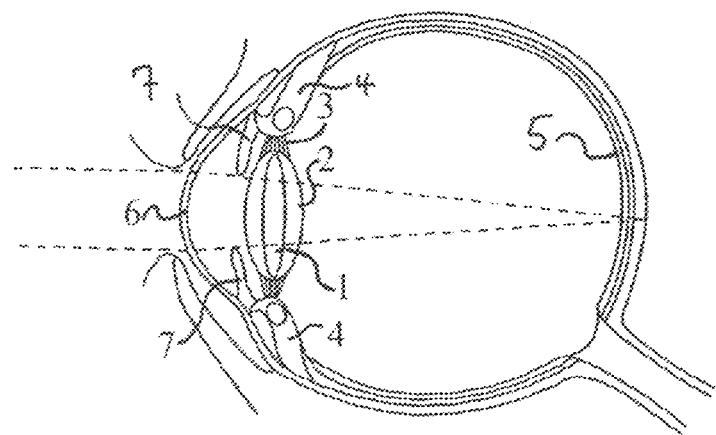
FIG. 2 shows an anterior to posterior cross sectional view of a human eye.

In the human eye, illustrated in FIG. 1 and FIG. 2, the lens 1 is contained within a capsule 2 and the capsule 2 is suspended by ligaments 3 from the ciliary body 4. The anterior of the eye consists of the cornea 6 with the pigmented tissue known as the iris 7. The lens 1 and the capsule 2 are formed of elastic tissue. The ciliary body 4 is a ring-like muscle which extends around the capsule 2 connected via zonule fibres 3 and which, when contracted, reduces the diameter of the capsule and the lens 1. This is achieved by releasing the tension created from the zonule fibres 3 being pulled taught between the ciliary muscles 4 and the capsule 2. When this tension is released by reducing the diameter of the ciliary muscles 4, the lens increases in thickness and its optical power is correspondingly increased so that objects a shorter distance from the eye are brought into sharper focus on the retina 5.

When the ciliary body 4 is relaxed, the elasticity of the capsule 2 and the lens 1 returns them to their original diameter, with the lens 1 now thinner and able to focus distant objects more clearly onto the retina 5. This change in optical power of the lens 1 is often referred to as "accommodation," and is necessary in order to bring objects at different distances from the lens 1 into sharp focus on the retina 5, because the distance between the lens 1 and the retina 5 is fixed.

The youthful eye has approximately 14 dioptres of accommodation. As a person ages, various factors combine to reduce the ability of the eye to accommodate to objects at differing distances. Firstly, the elasticity of the lens 1 and the capsule 2 reduces with age, making it more difficult for the ciliary body 4 to compress the lens 1 and capsule 2. Secondly, the ciliary body 4 may lose its elasticity, strength and effectiveness, reducing the ability of the ciliary body 4 to change the diameter of the capsule 2 and thus the optical power of the lens 1. This process commonly starts to occur at approximately 50 years of age, and the degree of accommodative capacity is sometimes reduced to as low as 2 dioptres. At a later age, the lens 1 may be considered non-accommodating, a condition referred to as presbyopia.

Apart from the age-related loss in ability to accommodate, intraocular lenses are also useful for treating cataracts. After placement of an intraocular lens, the accommodative process is no longer possible using a single element lens. There is tremendous need for the provision for an accommodative mechanism within an intraocular lens, thus restoring the accommodative capability of the recipient.

1. Variable Optical Strength Intraocular Lenses

IOLs of the present disclosure feature a variable optical strength that depends on the distance between a viewed object and the eye.

Referring generally to FIGS. 3 to 19, a variable optical strength intraocular lens 500 consistent with the present disclosure comprises a first lens element variably secured to a second lens element and a ciliary haptic complex in mechanical communication with the ciliary body 4 and at least one of the first lens element and the second lens element. The variable optical strength IOL 500 is characterized by an optical strength which varies in response to the contraction and relaxation of the ciliary body 4.

In some embodiments, a variable optical strength IOL 500 of the present disclosure comprises a lens complex 100 and a ciliary haptic complex 400 in mechanical communication with the lens complex 100.

Figure 3:
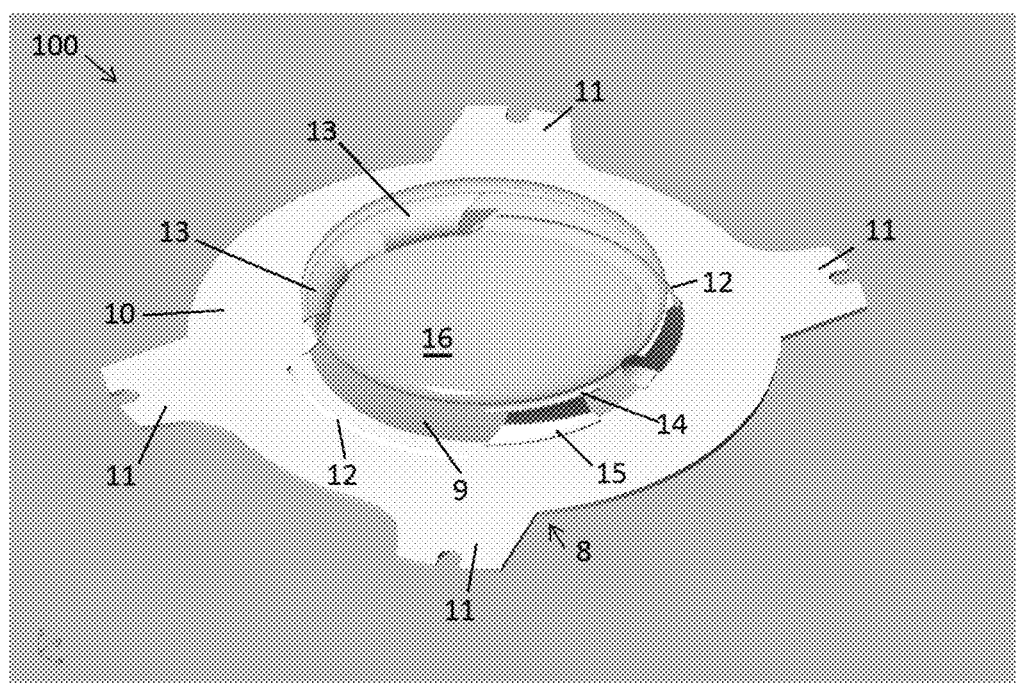
FIG. 3 shows a perspective view of a lens complex according to one embodiment of the present disclosure.
Figure 4:
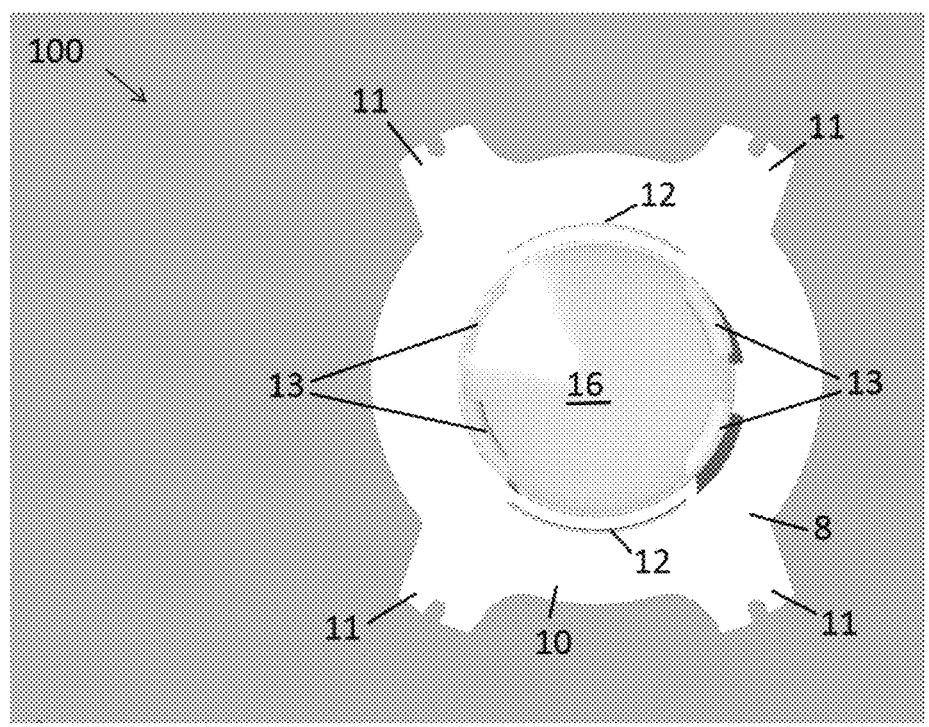
FIG. 4 shows a perspective view of the lens complex of FIG. 3 viewed from a superior angle.
Figure 5A:
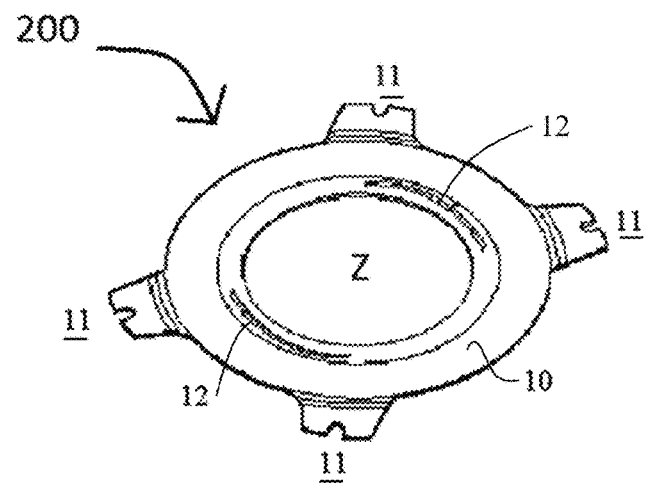
FIG. 5A shows an anterior-posterior perspective view of a lens complex according to one embodiment of the present disclosure.
Figure 5B:
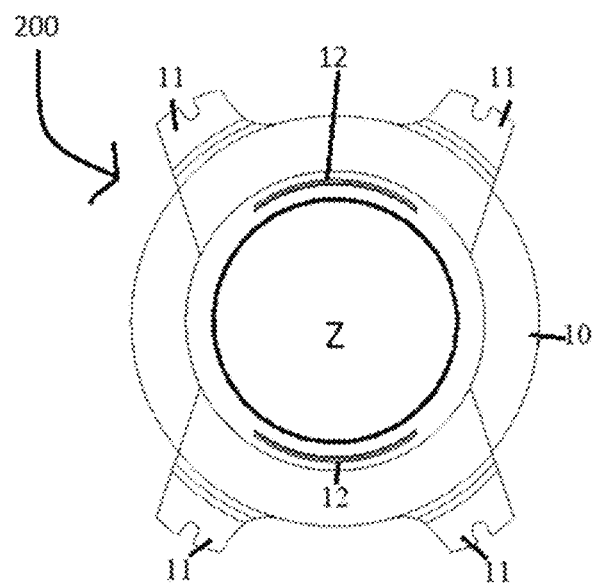
FIG. 5B shows another anterior-posterior perspective view of the lens complex of FIG. 5A.

Referring now to FIG. 3 and FIG. 4, the lens complex 100 may include a posterior segment 8, an anterior lens 16, and at least one spring 13 in operative communication with the posterior segment 8 and the anterior lens 16.

The posterior segment 8 includes a haptic plate 10 and a posterior lens 9. The haptic plate 10 is sized to fit within the capsular bag 2 of the eye. In some embodiments, the haptic plate 10 includes at least one capsular bag haptic 11 which is shaped to secure the haptic plate 10 within the capsular bag 2 in a particular orientation with respect to the ciliary muscles 4. As shown in FIG. 3, each of the at least one capsular bag haptics 11 may optionally include a notch. This arrangement allows the for spaces to be created between the capsular bag haptics 11, the edge of the haptic plate 10, and the capsular bag 2, allowing aqueous humour flow to persist substantially unimpeded. In addition, the capsular bag haptics 11 correctly anchor the posterior segment 8, and consequently the lens complex 100, at a central position within the capsular bag 2, aligning the lens complex 100 with the fovea on the retina 5.

In some embodiments, the haptic plate 10 includes at least one drainage slit 12 for enabling fluid to pass through the haptic plate 10. In some embodiments, the haptic plate 10 includes two drainage slits 12, which may be located at substantially opposing sides of the haptic plate 10. Alternatively, two or more drainage slits 12 may be located at any suitable location of the haptic plate 10.

During initial movement of the anterior lens 16 away from the posterior lens 9 in response to accommodation, the drainage slit(s) 12 may operate to supply aqueous humour into the inter-lens space. The functional implication of such a drainage passage is twofold; firstly the presence of aqueous fluid within the inter-lens space may function as an obstructive cushion of fluid preventing the anterior lens from fully reverting to its starting position upon dis-accommodation, preventing the variable optical strength IOL from appropriately refracting light based on the distance of the object observed. Secondly, the drainage slit(s) 12 enable continuous flow of aqueous fluid to the posterior surface of the posterior segment 8, feeding the network of double square edges and fluid channels 600 to guide aqueous fluid reducing or preventing posterior capsular opacification (PCO).

On one embodiment, the posterior lens 9 is located substantially at the center of the haptic plate 10. In some embodiments, the posterior lens 9 is stationary with respect to the haptic plate 10. In some embodiments, the posterior lens 9 and the haptic plate 10 are formed of a single piece of polymer. In other embodiments, the posterior lens 9 is a separate component from the haptic plate 10 and is secured to the haptic plate 10 using any suitable means. In such embodiments, the haptic plate 10 includes a void located substantially at its center to accommodate the posterior lens 9.

The posterior lens 9 may have any suitable shape. In some embodiments, the posterior lens has a biconcave shape. In other embodiments, the posterior lens 9 has a biconvex shape. In other embodiments, the posterior lens 9 has a concave shape. In other embodiments, such as those shown illustratively in the accompanying figures, the posterior lens 9 has a convex shape.

Figure 9A:
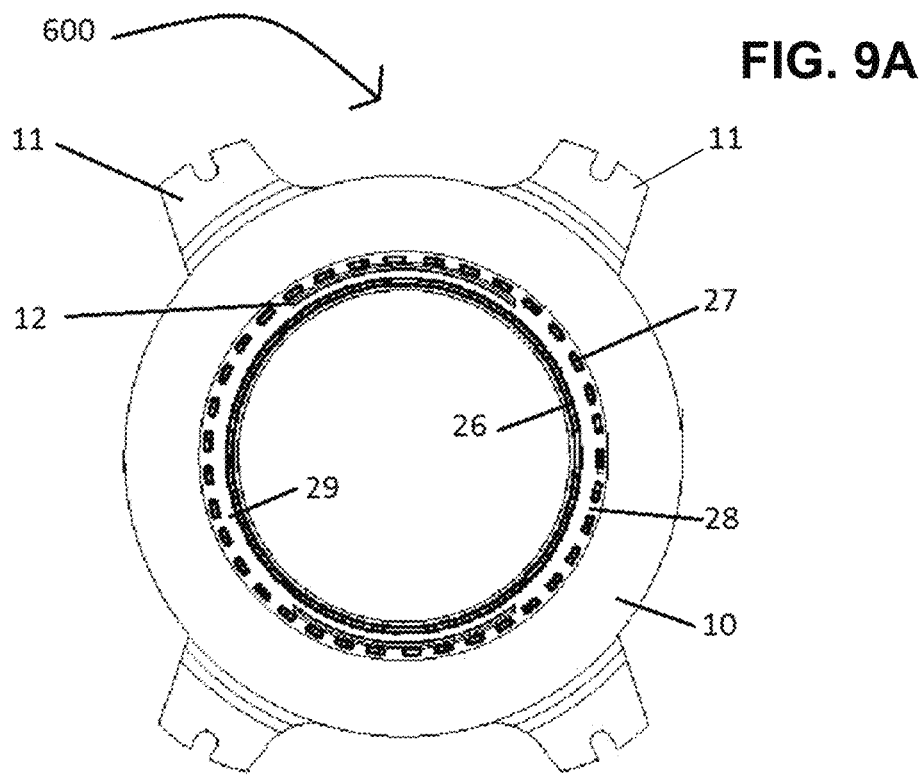
FIG. 9A shows view of the posterior surface of the posterior segment of a lens complex according to one embodiment of the present disclosure.
Figure 9B:
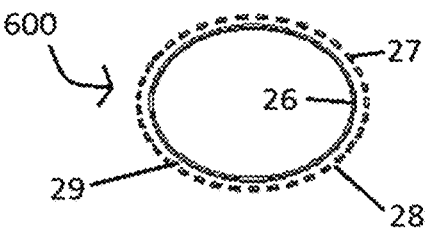
FIG. 9B shows a perspective view of square edges and an inter-squared edge channel of the posterior segment of FIG. 9A.
Figure 10:
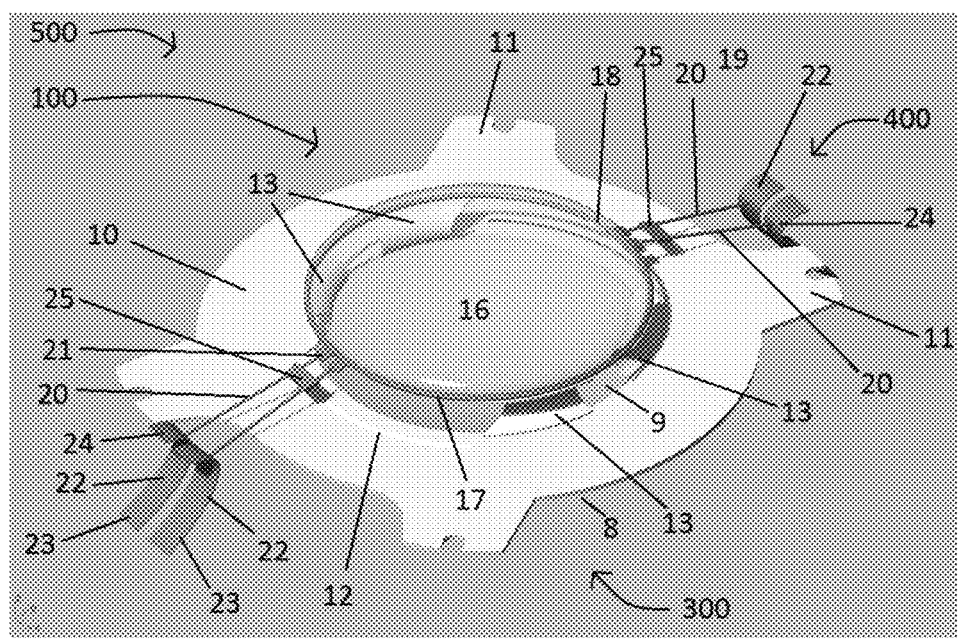
FIG. 10 shows a perspective view of a variable optical strength intraocular lens including a lens complex and a ciliary haptic complex coupled together.
Figure 11:
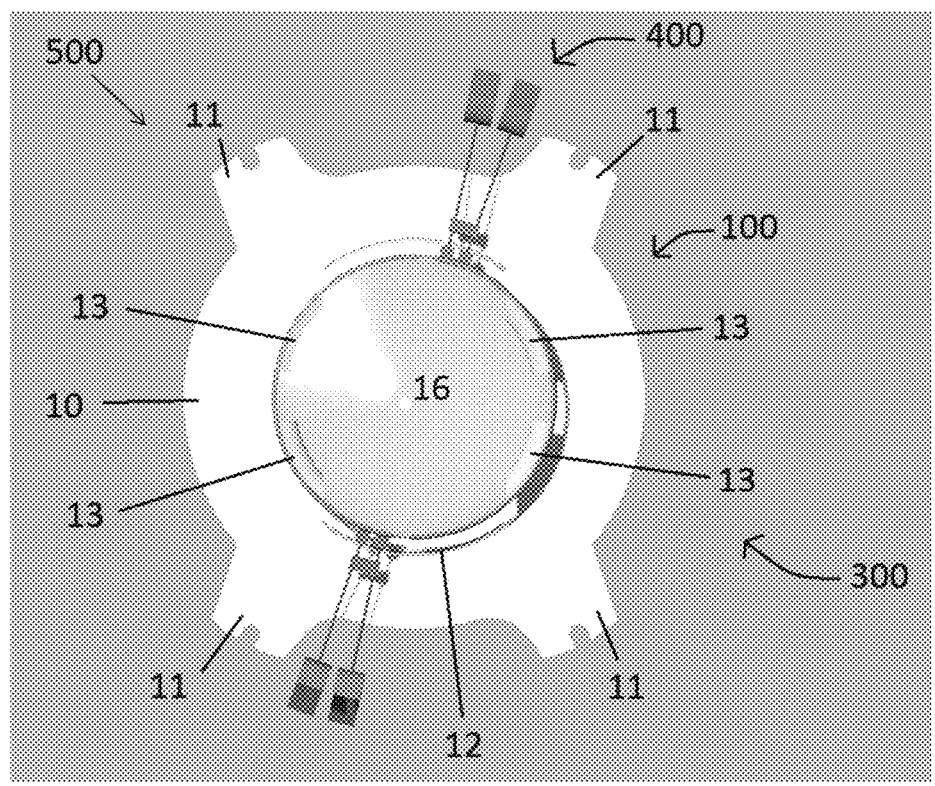
FIG. 11 shows an anterior posterior view of the variable optical strength intraocular lens of FIG. 10.
Figure 12:
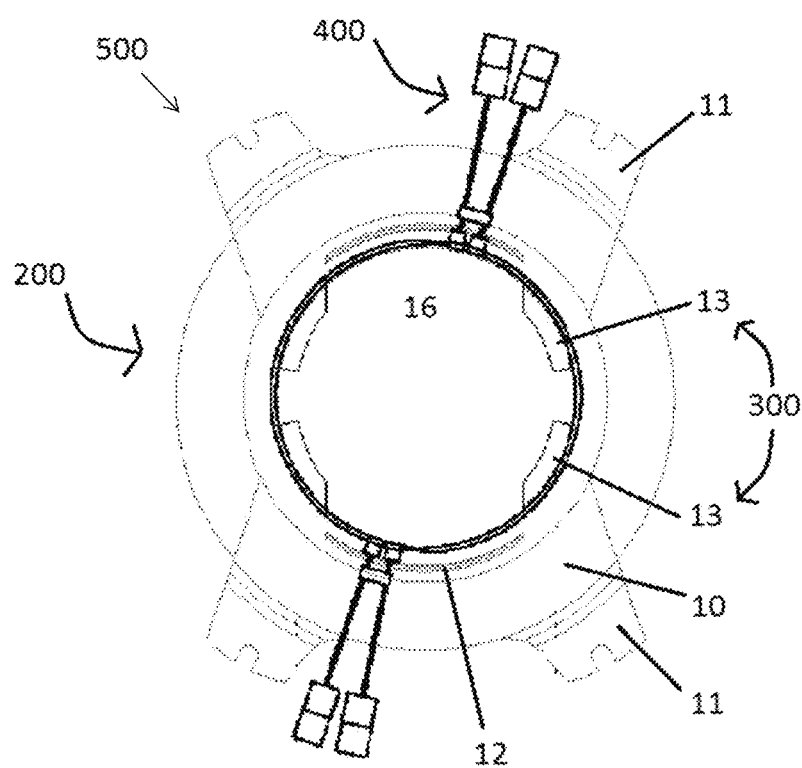
FIG. 12 shows an anterior posterior view of the variable optical strength intraocular lens of FIGS. 10-11.
Figure 13:
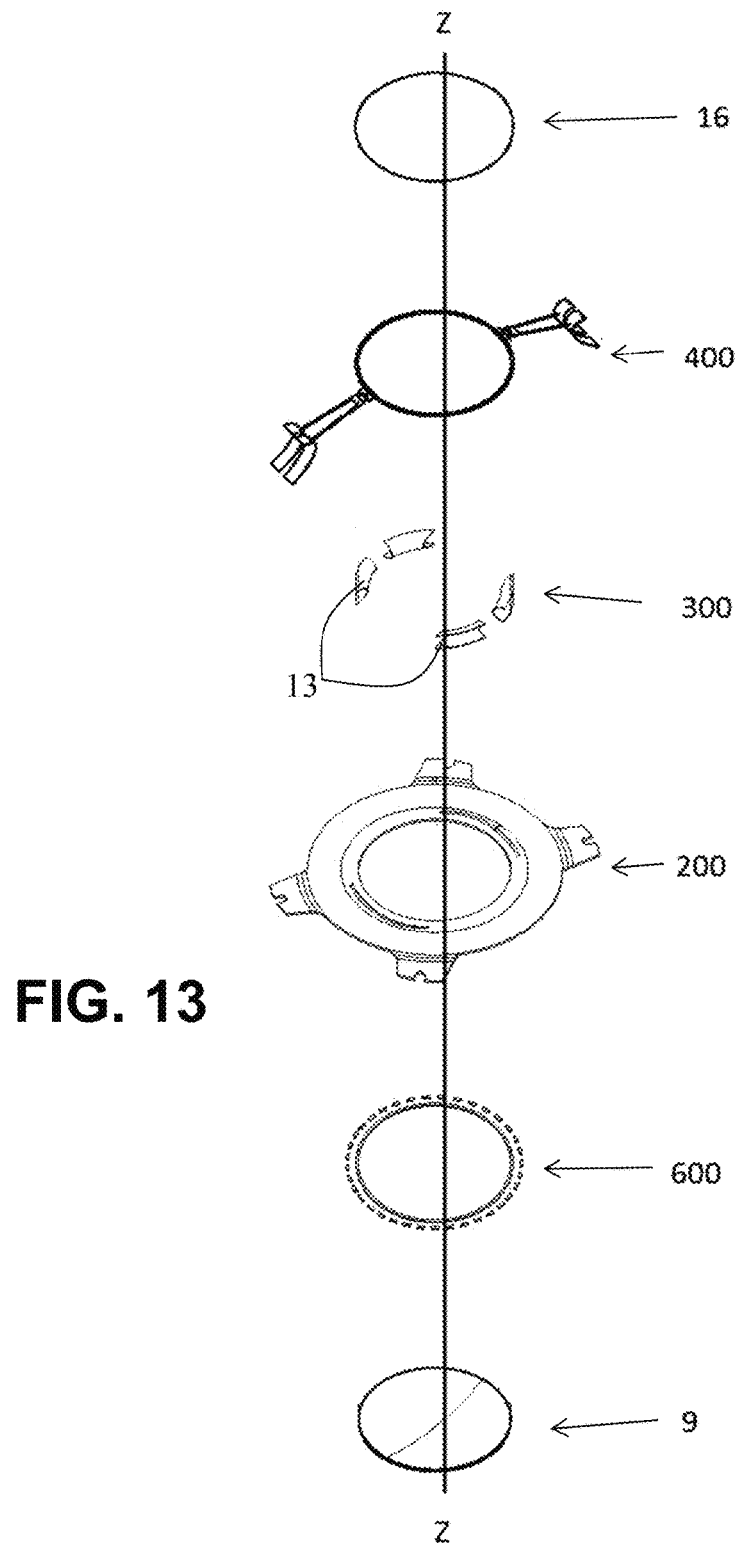
FIG. 13 shows an exploded perspective view of various components of a lens complex and a ciliary haptic complex according to one embodiment of the present disclosure.
Figure 15:
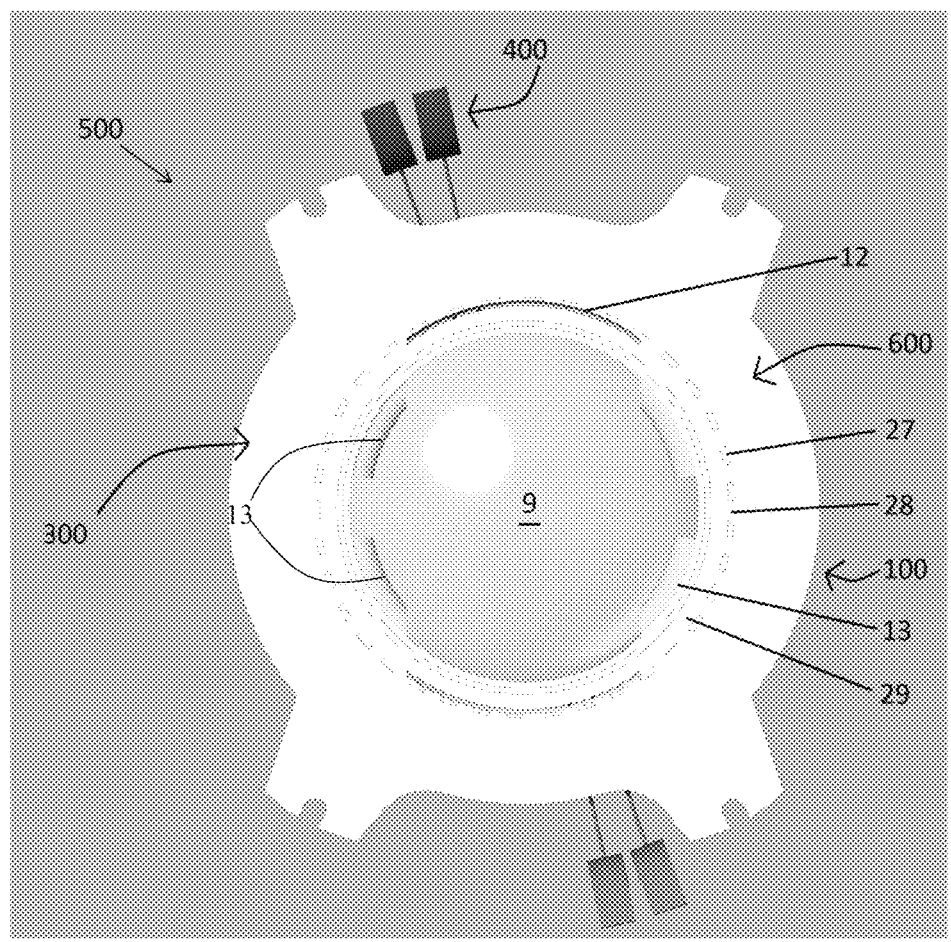
FIG. 15 shows an inferior view of a variable optical strength intraocular lens according to one embodiment of the present disclosure.

Referring now to FIGS. 9A-9B, in some embodiments the posterior surface of the haptic plate 10 includes a posterior capsular opacification (PCO) prevention system 600. The PCO prevention system 600 impedes regrowth of epithelial tissue in the region of the 'equator' of the capsule along the resurface of the posterior segment 8. In some embodiments, the PCO prevention system 600 may include an inner squared edge 26 surrounding the optical zone and/or the posterior lens 9, an outer squared edge 27 encircling the inner squared edge 26, and an inter-squared edge channel 29 between the inner squared edge 26 and the outer squared edge 27. In some embodiments, the outer squared edge 27 includes one or more interruptions 28 which allow fluid to pass therethrough. In one embodiment, fluid flows out via the interruptions 28 and into the space surrounding the outer square edge.

Figure 16:
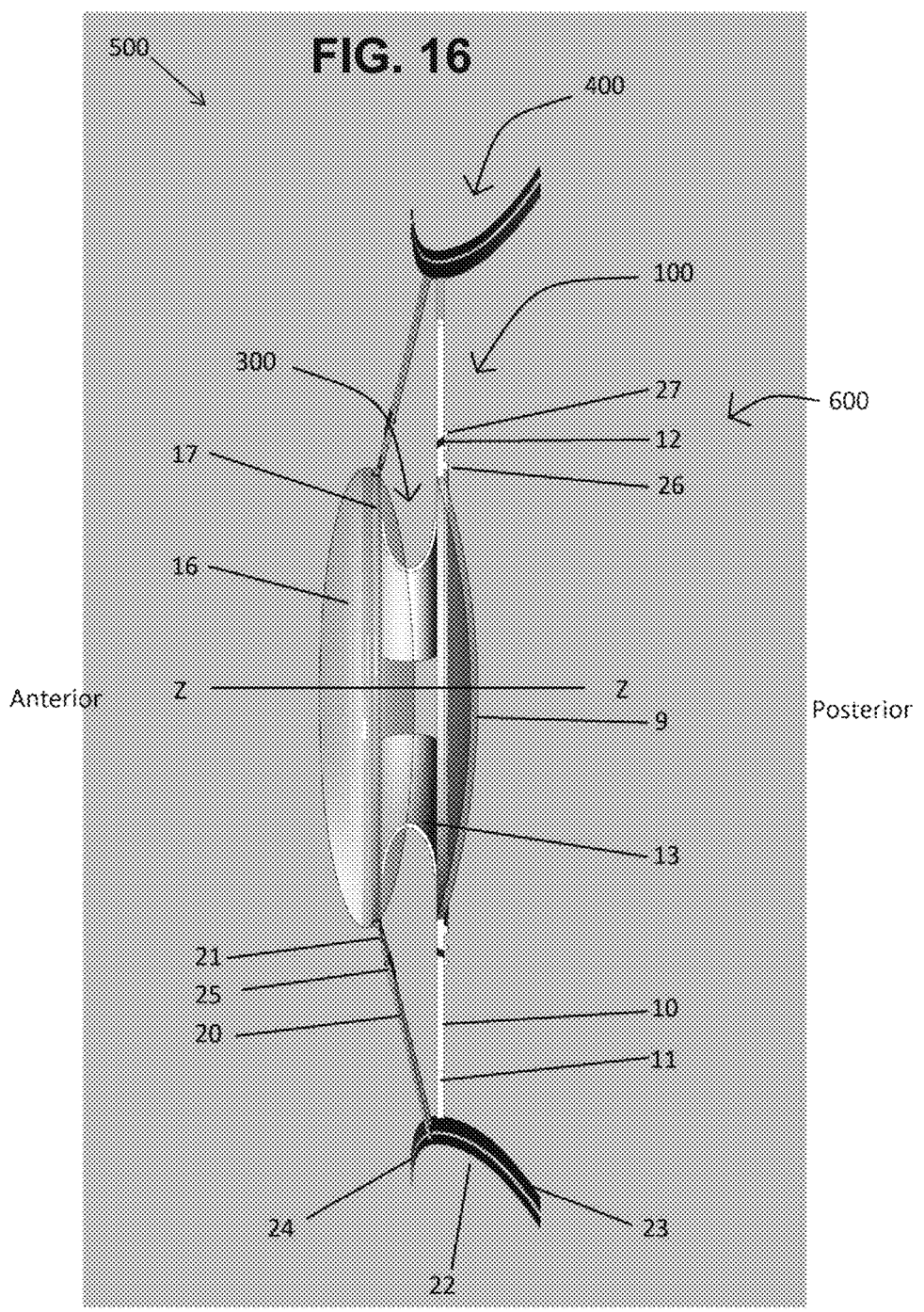
FIG. 16 shows a lateral perspective/cross-sectional view of a coupled lens complex and ciliary haptic complex according to one embodiment of the present disclosure.
Figure 17:
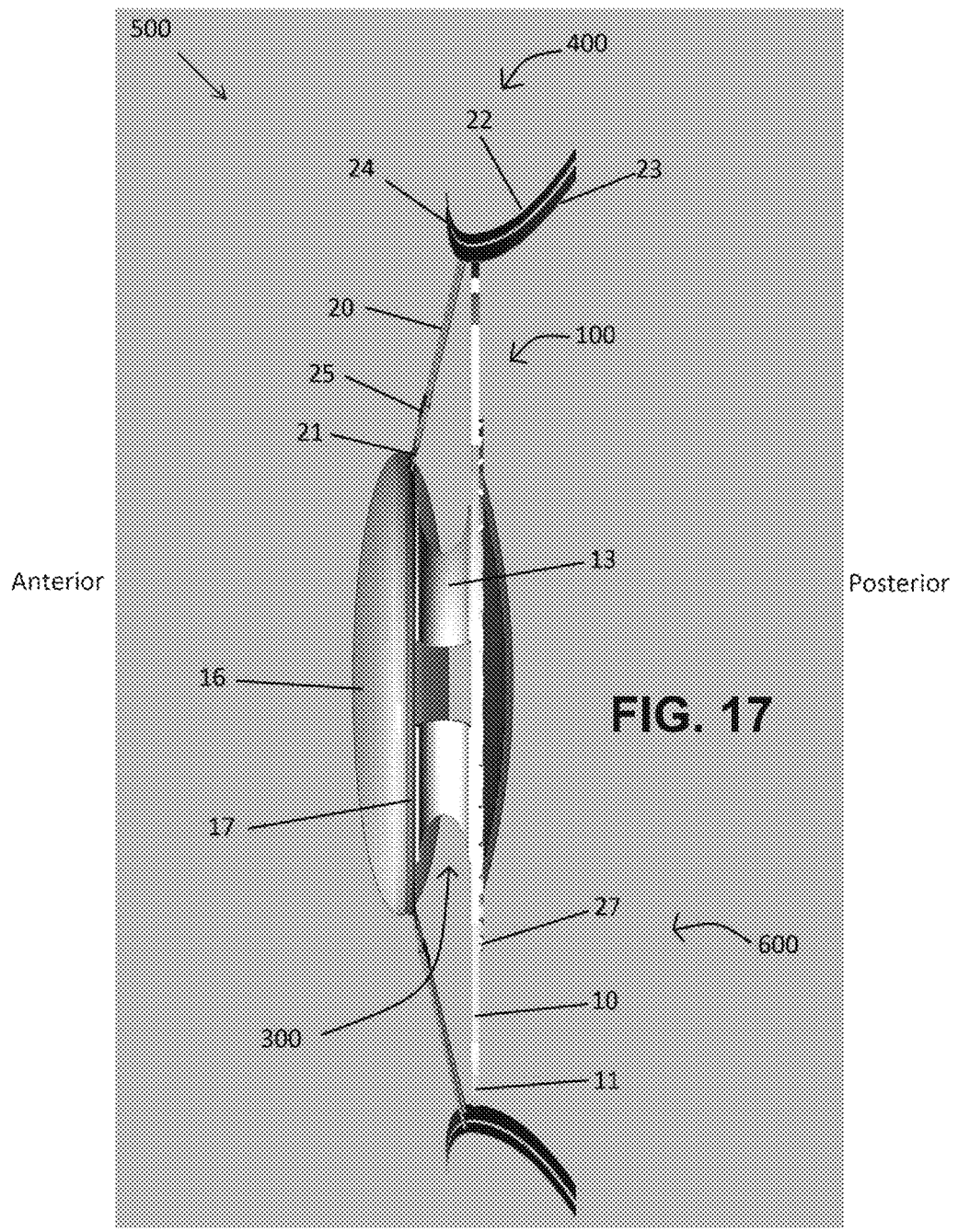
FIG. 17 shows a lateral perspective/cross-sectional view of the coupled lens complex and ciliary haptic complex of FIG. 16.
Figure 18:
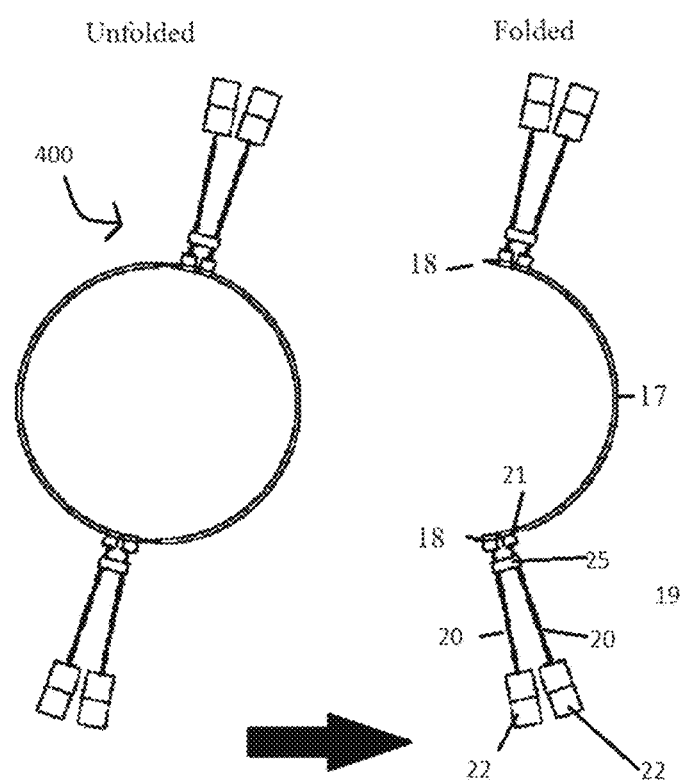
FIG. 18 shows transition of a ciliary haptic complex from an unfolded configuration to a folded position according to one embodiment of the present disclosure.

In some embodiments, the one or more drainage slits 12 may be located in the inter-squared edge channel 29, for example as shown in FIG. 9A. The combination of the drainage slit(s) 12 and the PCO prevention system 600 thus reduced the likelihood that a secondary cataract will form in the optical zone. Without wishing to be bound by theory, it is postulated that compression of fluid between the anterior lens 16 and the posterior lens 9 forces fluid to vacate the inter-lens space in every direction, including through the drainage slit(s) 12 which in some embodiments may be formed at an angle relative to the surfaces of the haptic plate 10 in order to more efficiently drain fluid away from the central optical zone. For example, as shown in FIG. 16, the drainage slit(s) 12 are formed at an angle that forces fluid away from the optical zone Z as it moves through the drainage slit(s) 12 from the superior side of the haptic plate 10 to the inferior side of the haptic plate 10.

Fluid drained through the drainage slit(s) 12 may be funneled into and along the inter-squared edge channel 29.

In embodiments including a drainage slit 12 above the optical zone Z (a superior drainage slit 12) and a drainage slit below the optical zone Z (an inferior drainage slit 12), such as the embodiment shown in FIG. 16, the direction of fluid flow along the inter-squared edge channel 29 depends from which drainage slit 12 the fluid enters the channel 29. For example, fluid entering via a superior drainage slit 12 will tend to drain in the inferior direction along the inter-squared edge channel 29, whereas fluid drained from the inferior drain will tend to flow superiorly in along the inter-squared edge channel 29 to the equatorial mark. The squared edge interruptions 28 also assist in encouraging drainage of fluid from the inter-squared edge channel 29 by acting as exit channels to the space surrounding the outer squared edge 27. The continuous outpouring of fluid via the squared channel interruptions 28 thus provides an extra barrier to the migration of cells along the posterior segment 8 and the posterior lens 9 as the continuous push back of fluid away from the central optical zone Z discourages or prevents approach or encroachment of the cells and thus a secondary cataract.

In one embodiment, the anterior lens 16 is a separate component from the posterior lens 9, and is typically a bi-convex lens. The anterior lens 16 is secured to the haptic plate 10 or to the posterior lens 9 by the spring(s) 13. This arrangement enables the anterior lens 16 to move along an axis parallel to the optical zone Z with respect to the anterior lens 9.

In one embodiment, the anterior lens 16 is shaped in vertical section like an oval, with a thicker central region and a thinner peripheral region. The bi-convex nature of the anterior lens 16 allows it to abut closely on the superior arm 14 of the one or more springs 13. In one embodiment, the anterior lens 16 is marginally wider than the central optical zone of the posterior segment 8, allowing for a degree of overhang when compared to the circumference created by the outer edge of the superior arms 14 of the springs 13 (see FIG. 15). The wider diameter of the anterior lens 16 in comparison to the diameter of the central ring of the ciliary haptic complex 400 provides a locking mechanism for the lens complex 100 and the ciliary haptic complex 400, and enables continued coupling of the two complexes to ensure correct separation of the anterior lens 16 and the posterior lens 9.

The one or more springs 13 may comprise any shape and material suitable to enable the anterior lens 16 to move relative to the posterior lens 9. For example, as especially shown in FIG. 6, the one or more springs 13 may include a C-shaped cross section defined by a superior arm 14 and an inferior arm 15.

Figure 6:
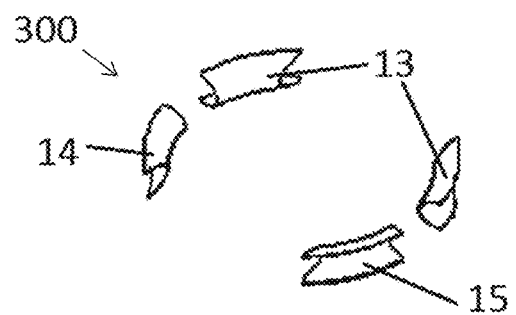
FIG. 6 shows a perspective view of one arrangement of a plurality of C-shaped spring components of a lens complex according to one embodiment of the present disclosure.
Figure 19:
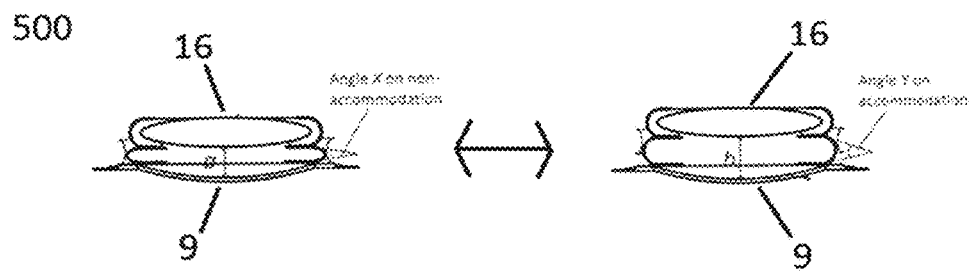
FIG. 19 shows a change in optical strength of a variable optical strength intraocular lens during accommodation and non-accommodation according to one embodiment of the present disclosure.
Figure 20:
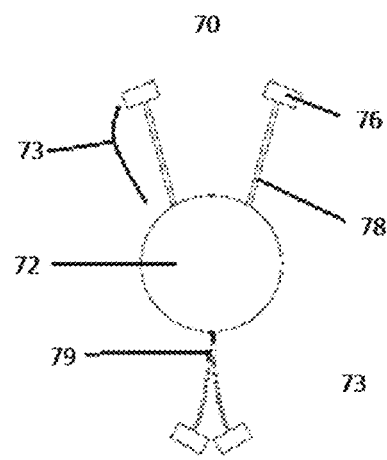
FIG. 20 shows a top view of an anterior lens segment according to one embodiment of the present disclosure.
Figure 21:
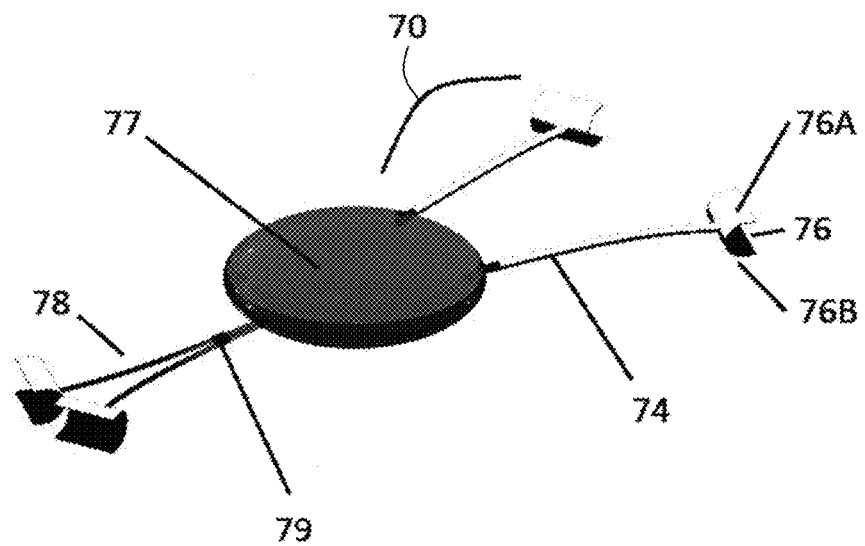
FIG. 21 shows a perspective view of an anterior lens segment according to one embodiment of the present disclosure.
Figure 22:
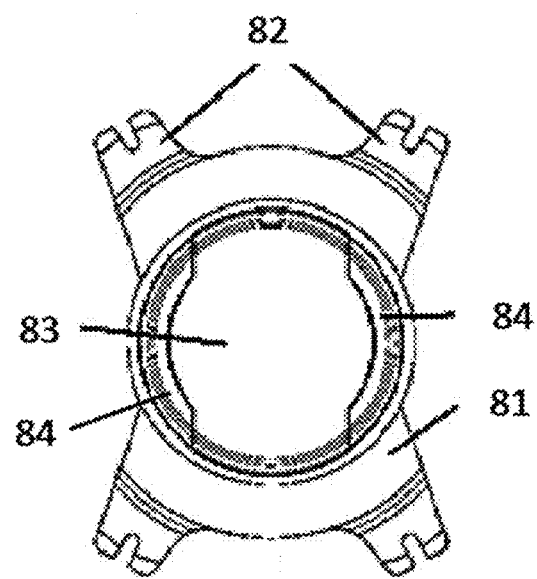
FIG. 22 shows a top view of a posterior lens segment according to one embodiment of the present disclosure.
Figure 23:
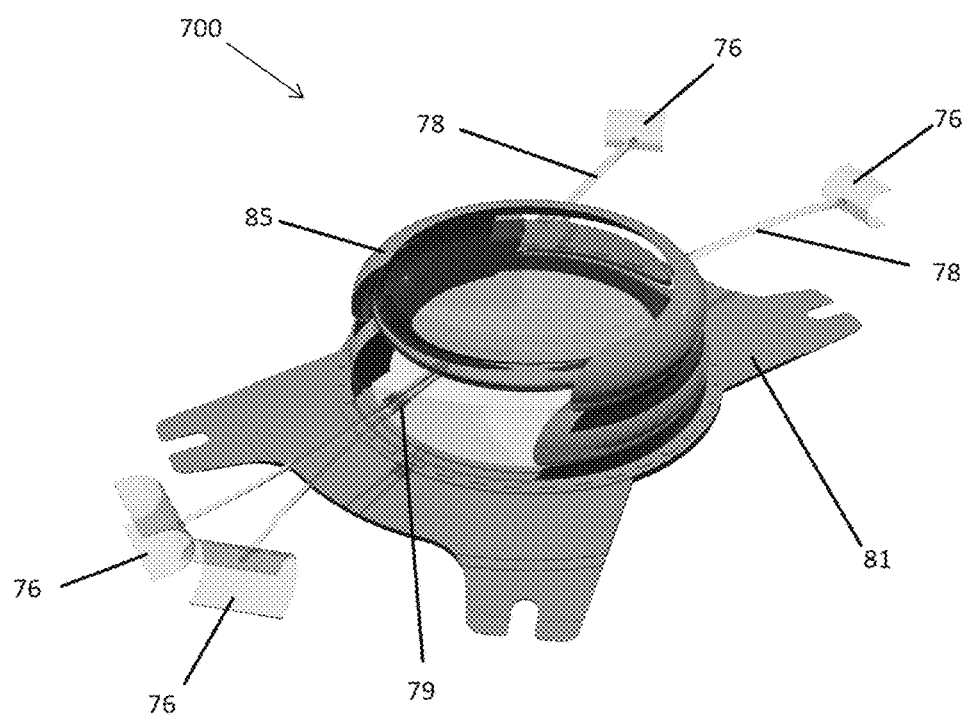
FIG. 23 shows a perspective view of an intraocular lens complex according to one embodiment of the present disclosure.
Figure 24:
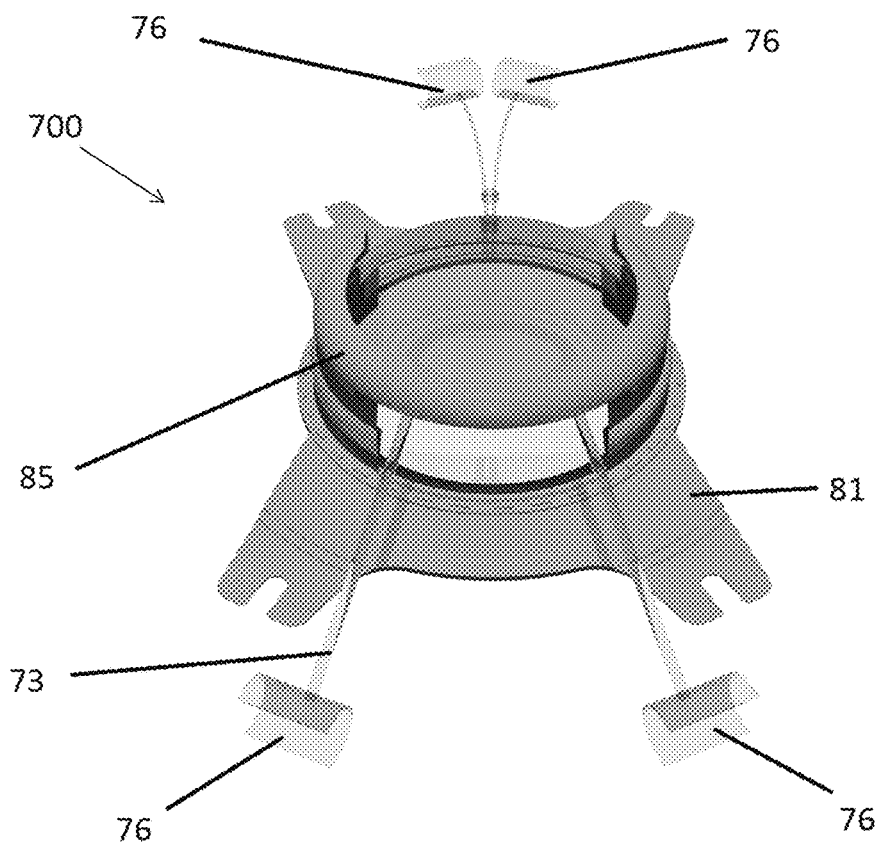
FIG. 24 shows a perspective view of an intraocular lens complex according to one embodiment of the present disclosure.
Figure 25:
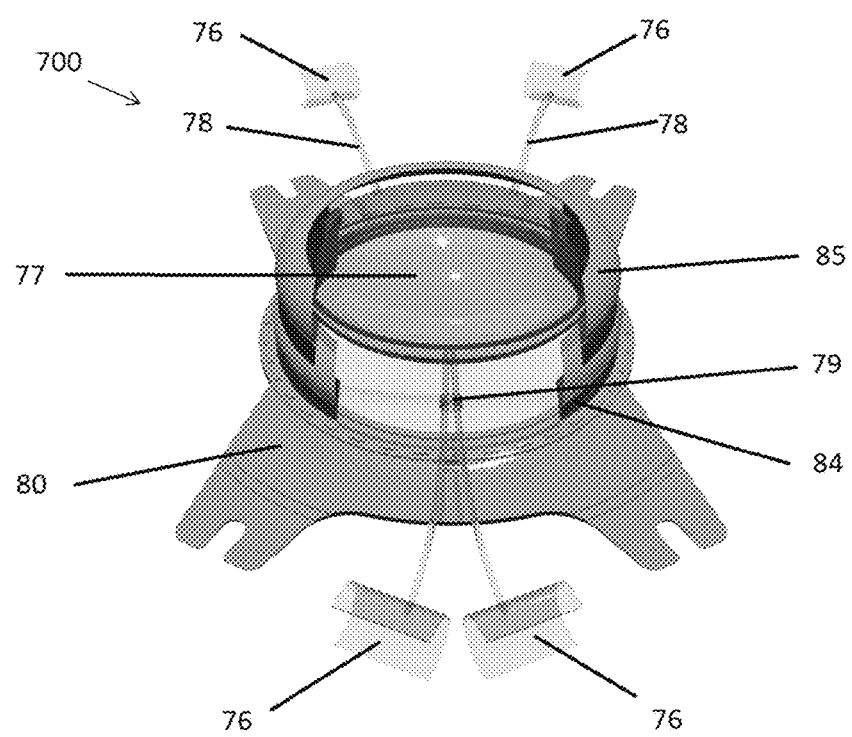
FIG. 25 shows a perspective view of an intraocular lens complex according to one embodiment of the present disclosure.
Figure 26:
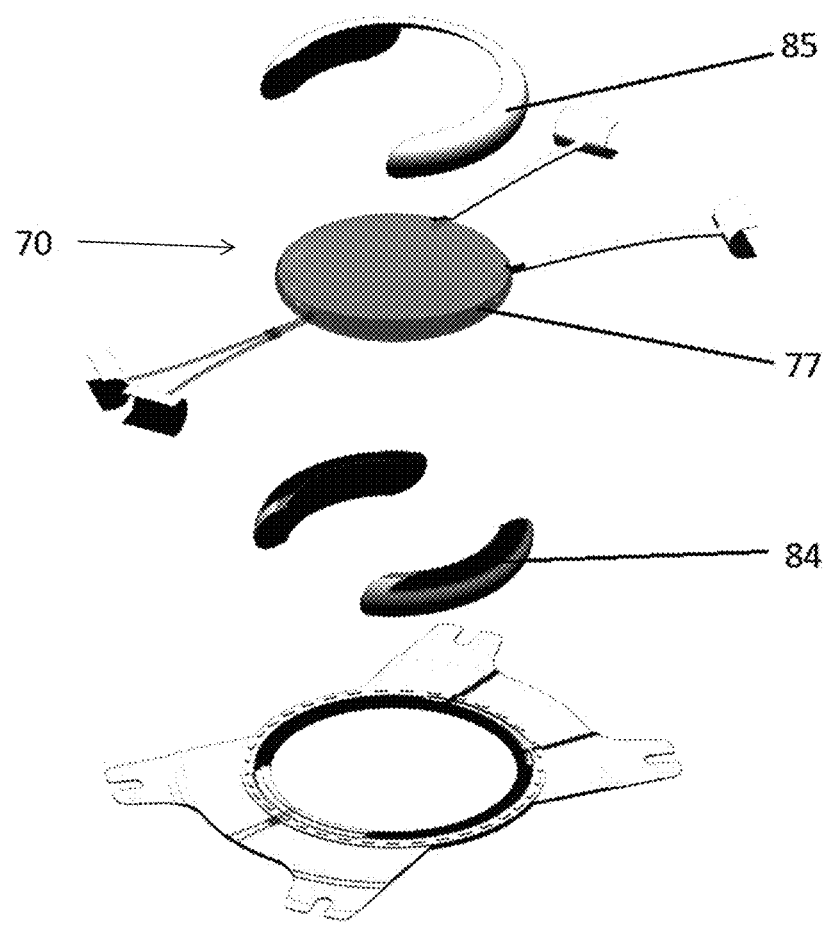
FIG. 26 shows a perspective view of various components of an intraocular lens complex according to one embodiment of the present disclosure.

Collectively, the one or more springs 13 may be referred to as the spring complex 300. As shown in FIGS. 6 and 19, the spring complex 300 may include any number of springs 13 arranged in any suitable configuration to enable the anterior lens 16 to move relative to the posterior lens 9 while keeping the anterior lens 16 parallel to the anterior lens 9 regardless of the distance a or b between the lenses. In one embodiment, accommodation forces imparted on the lens complex 100 by the ciliary muscles 4 cause an increase in the distance between the anterior lens 16 and the posterior lens 9, for example from a first distance a without accommodation forces to a second, larger distance b in response to accommodation forces from the ciliary muscles 4, without altering the horizontal orientation (e.g., tilt) of the anterior lens 16 relative to the posterior lens 9. In some embodiments, the spring complex 300 includes one spring 13. In other embodiments, the spring complex includes two springs 13, optionally wherein the two springs are located substantially opposite each other with respect to the circumference of the anterior lens 16. In still other embodiments, the spring complex 300 includes three springs 13 arranged substantially evenly with respect to the circumference of the anterior lens 16 (e.g., separated by about 120° each around the anterior lens 16 circumference). In other embodiments, the spring complex 300 includes four springs 13 arranged substantially evenly with respect to the circumference of the anterior lens 16 (e.g., separated by about 90° each around the anterior lens 16 circumference).

In some embodiments, such as those shown in FIGS. 3, 4, 6, 10-17, the spring complex 300 includes four springs 13 arranged in a non-uniform manner about the circumference of the anterior lens 16. In some embodiments, the four springs 13 may be arranged in a manner such that the separation between adjacent springs 13 alternates between a first, large separation and a second, small separation. For example and without limitation, adjacent springs 13 may be separated from each other by about 60°, about 120°, about 60°, and about 120° respectively with respect to the circumference of the anterior lens 16.

Figure 7:
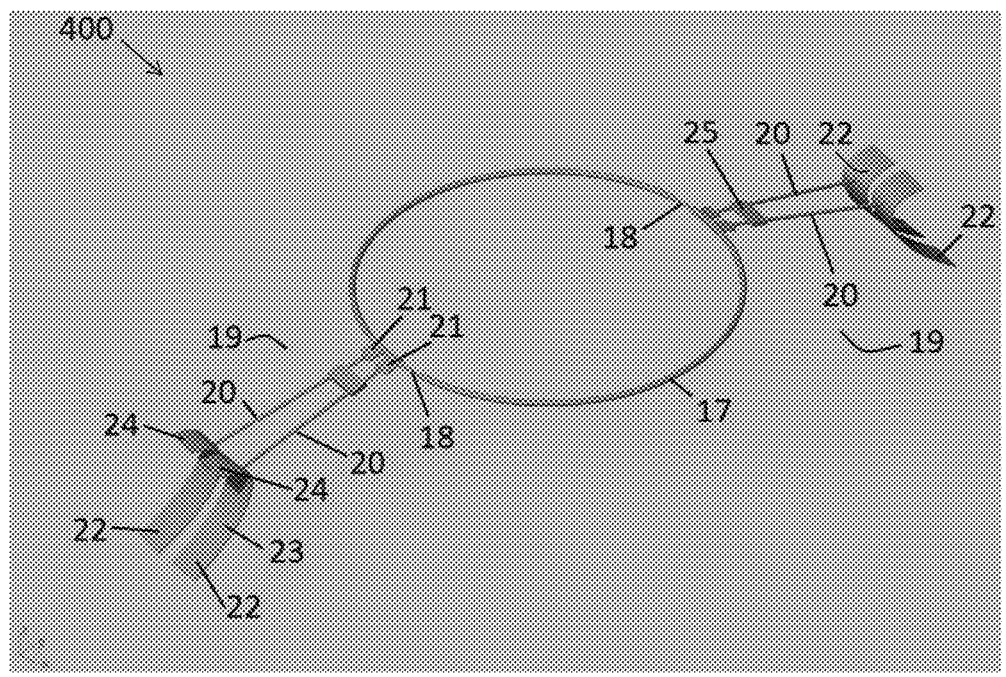
FIG. 7 shows a perspective view of a ciliary haptic complex according to one embodiment of the present disclosure.

Referring now generally to FIGS. 7-8B, in one embodiment the ciliary haptic complex 400 includes a central ring 17 and at least one ciliary haptic 19. Typically, the ciliary haptic complex 400 includes two ciliary haptics 19. In embodiments wherein the ciliary haptic complex 400 includes more than one ciliary haptics 19, the ciliary haptics 19 may be arranged substantially symmetrically about the central ring 17.

In one embodiment, the central ring 17 is sized slightly smaller than the anterior lens 16. The central ring 17 may be formed of a material having a substantially uniform cross-sectional area or diameter. Alternatively, the central ring 17 may include two discrete areas having a smaller diameter 18 than the remaining portions of the central ring 17. The two discrete areas of smaller diameter 18 define a folding zone along which the central ring 17 may be folded for convenient injection into the capsular bag 2. In some embodiments, the two discrete areas of smaller diameter 18 are located substantially opposite each other with respect to the central ring 17 such that the ciliary haptic complex 400 may adopt a folded configuration having a minimized width, as shown representatively in FIG. 18.

In one embodiment, each ciliary haptic complex 19 includes one or two ciliary muscle plates 22 for placement against the ciliary muscles 4. In some embodiments, the ciliary muscle plate 22 has a generally C-shaped cross-sectional shape, which may include a short arm 24 and a long arm 23. In some embodiments, the short arm 24 is located on the superior portion of the ciliary muscle plate 22, while the long arm 23 is located on the inferior portion of the ciliary muscle plate 22. This particular configuration provides secure engagement with the ciliary muscles 4, as the long arm 24 is substantially complementary to the ciliary muscle protrusion to which the zonule fibres 3 attach, while enabling the long arm 23 to closely engage with the ciliary muscle 4.

In one embodiment, each ciliary haptic complex 19 further includes one ciliary haptic shaft 20 connecting the ciliary muscle plate 22 to the central ring 17. The ciliary haptic shaft 20 provides structural support to the lens complex 100 by connecting the anatomy to the lens complex 100. In addition, the ciliary haptic shaft 20 acts as the force conduit, transferring the accommodation forces from the ciliary muscles 4 to the anterior lens 16 via the central ring 17. The ciliary haptic shaft 20 may be formed of any suitable material and may feature any cross-sectional shape. In some embodiments, the ciliary haptic shaft 20 is cylindrical in shape, with a substantially uniform ovoid or circular cross-sectional shape throughout.

In one embodiment, the ciliary haptic shafts 20 have a length that enables them to assume a slightly arched configuration upon implantation, wherein the arch bends away from the iris 7 and towards the posterior of the eye. This arched shape assists in guiding the captured contractive force of the ciliary muscle 4 to the central ring 17 via the ciliary muscle plates 22. The angulation of the ciliary haptic shafts 20 towards the anterior lens 16 and by way of imaginary extension towards the pupil assists in pushing the central ring 17 and consequently the anterior lens 16 towards the pupil as the ciliary muscle plates 22 move centrally.

If the length of the ciliary haptic 19 equals a perpendicular length (unaccommodated), the ciliary haptic 19 is not under any compressive force until accommodation occurs. In such a configuration, the central ring 17 and the anterior lens 16 do not vault away from the posterior lens 9 at rest. Such a phenomenon is termed myopic shift and provides an undesirable increased degree of refraction in the non-accommodated position. However, if the length of the ciliary haptic 19 is longer than the perpendicular (unaccommodated) length, the ciliary muscle plates 22 will exert some force onto the ciliary haptic shafts 20 which, in turn, will vault the central ring 17 and the anterior lens 16 slightly forward even without accommodating forces imparted on the ciliary haptics 19 at the starting position, with further visually inappropriate vaulting on accommodation.

The length of the ciliary haptic shafts 20 may be fixed (e.g., non-adjustable). Alternatively, as shown representatively in FIGS. 7, 8, 10, 12, 14 and 16-18, the ciliary haptics 19 may include an adjustment band 25 that allows the relative lengths of the ciliary haptic shafts 20 to be adjusted by enabling larger or smaller separations of adjacent pairs of ciliary muscle plates 22. For example, in embodiments wherein the adjustment band 25 is slidably associated with a pair of ciliary haptic shafts 20, such as in the embodiments shown in FIGS. 7, 8, 10-14 and 16-18, positioning the adjustment band 25 near the ciliary muscle plates 22 forces the pair of ciliary muscle plates 22 to engage with portions of the ciliary muscle 4 that are near each other. In this configuration, the ciliary haptic 19 is overall relatively rigid. Conversely, positioning the adjustment band 25 near the central ring 17 allows the ciliary muscle plates 22 to engage with relatively separated portions of the ciliary muscle ring 4. The resulting ciliary haptic 19 is much more flexible, and allows adjustment of the variable optical strength IOL 500 upon implantation such that the anterior lens 16 is not overly vaulted away from the posterior lens 9 when the ciliary muscles 4 are in a relaxed (non-contracting, non-accommodating) state. In other words, the adjustment band(s) 25 enable the customization of a variable optical strength IOL 500 as disclosed herein to each individual patient's unique anatomy to avoid myopic shift.

In one embodiment, each ciliary haptic 19 intersects the central ring 17 at an attachment zone 21. In some embodiments, the attachment zones 21 are offset from the discrete areas of smaller diameter 18 such that the ciliary haptics 19 do not impede folding of the central ring 17 along the folding zone.

In some embodiments, the attachment zones 21 span between the proximal edge of the ciliary haptic shaft 20 and the central ring 17. In some embodiments, the material used to form the central ring 17 is the same as the material used to form the ciliary haptic shafts 20. In some embodiments, the attachment zones 21 have a rectangular cross section. In one embodiment, the proximal portion of the attachment zones 21 of all the ciliary haptics 19 contact and fuse with the central ring 17, thus creating a single solid complex central ring 17 with ciliary haptics 19 connected via the attachment zones 21. In one embodiment, the flat and wide nature of the attachment zones 21 facilitates seamless anterior vaulting of the central ring 17 by permitting a degree of bending and flexing such that the proximal portion of the ciliary haptics 19 (e.g., the proximal portion of each ciliary haptic shaft 20) may vault anteriorly with flexing of the central ring 17 to push the anterior lens 16 in the same direction as the vaulting of the ciliary haptics 19.

FIGS. 10-17 illustrate coupling of the lens complex 100 and the ciliary haptic complex 400 to form the variable optical strength IOL 500. In one embodiment, the central ring 17 of the ciliary haptic complex 400 is positioned against the inferior side of the anterior lens 16. In this configuration, inward force on the ciliary haptics 19 force the central ring 17 away from the posterior lens 9, which pushes the anterior lens 16 away from the posterior lens 9 and against the pull of the spring(s) 13 of the spring complex 300. Conversely, discontinuation of an inward force on the ciliary haptics 19 cause the anterior lens 16 to move toward the posterior lens 9 in response to tension of the spring(s) 13 of the spring complex 300. The ciliary haptics 19 are simultaneously pushed outward as the central ring 17 is forced towards the posterior lens 9 by the returning anterior lens 16.

In some embodiments, the present disclosure provides a variable optical strength intraocular lens 500 comprising (i) a lens complex 100 comprising an anterior segment comprising an anterior lens 16, a posterior segment 8 comprising a posterior lens portion 9 and a haptic plate portion 10, wherein the haptic plate portion 10 substantially surrounds an optical zone Z, and at least one spring 13 in contact with the anterior segment 8 and the posterior segment to provide a separation distance between the anterior lens 16 and the posterior lens 9; and (ii) a ciliary haptic complex 400 comprising a central ring 17, a first ciliary muscle haptic 19 extending outwardly from the central ring 17, and a second ciliary muscle haptic 19 extending outwardly from the central ring 17, wherein upon insertion into an eye, the central ring 17 is in contact with an inferior side of the anterior lens 16 and the first and second ciliary muscle haptics 19 are in communication with ciliary muscle 4 of the eye. In some embodiments, contraction of the ciliary muscle 4 causes the separation distance between the anterior lens 16 and the posterior lens 9 to increase. In some embodiments, the at least one spring 13 comprises one, two, three, four, or more than four springs 13 having a C-shaped cross-section. In some embodiments, the haptic plate portion 10 comprises a drainage slit 12. In some embodiments, a posterior surface of the posterior segment 8 comprises a continuous inner squared edge 26 surrounding the optical zone Z, an interrupted outer squared edge 27 surrounding the continuous inner squared edge 26, and an inter-squared edge channel 29 between the continuous inner squared edge 26 and the interrupted outer squared edge 27 for accommodating aqueous fluid upon insertion into an eye. In some embodiments, the first and second ciliary muscle haptics 19 each comprise at least one ciliary muscle plate 22 at a peripheral end. In some embodiments, the first and second ciliary muscle haptics 19 each comprise a first ciliary muscle plate 22 connected to the central ring 17 by a first ciliary haptic shaft 20 and a second ciliary muscle plate 22 connected to the central ring 17 by a second ciliary haptic shaft 20. In some embodiments, each pair of first and second ciliary haptic shafts 20 further includes an adjustment band 25 for enabling adjustment of a length of each pair of first and second ciliary haptic shafts 20. In some embodiments, the at least one ciliary muscle plate 22 has a C-shaped cross-sectional area. In some embodiments, each of the at least one ciliary muscle plate 22 having a C-shaped cross-sectional area comprises a first anterior segment 24 and a second posterior segment 23, wherein the second posterior segment 23 is longer than the first anterior segment 24. In some embodiments, the central ring 17 comprises two discrete areas of primary thickness and two discrete areas of secondary thickness 18, wherein the two discrete areas of secondary thickness 28 have a smaller diameter than the two discrete areas of primary thickness. In some embodiments, the two discrete areas of secondary thickness 18 are located at substantially opposing regions of the central ring 17 to define a folding zone. In some embodiments, a junction between the first ciliary haptic shaft 20 and the central ring 17 and a junction between the second ciliary haptic shaft 20 and the central ring 17 define attachment zones 21, and wherein the two discrete areas of secondary thickness 18 are offset from the attachment zones 21. In some embodiments, the haptic plate portion 10 further comprises at least one capsular bag haptic 11 at a peripheral edge. In some embodiments, the haptic plate portion 10 comprises four capsular bag haptics 11 arranged about the peripheral edge. In some embodiments, the lens complex 100 is formed of a hydrophobic acrylic. In other embodiments, the lens complex 100 is formed of a hydrophilic acrylic. In other embodiments, the lens complex 100 is formed of a silicone. In other embodiments, the lens complex 100 is formed of a combination of a hydrophobic acrylic, a hydrophilic acrylic, and a silicone. In some embodiments, the ciliary haptic complex 400 is formed of a polymethylmethacrylate. In other embodiments, the lens complex 100 is formed of a polyamide of low hydration. In other embodiments, the lens complex 100 is formed of a hydrophobic acrylic. In other embodiments, the lens complex 100 is formed of a hydrophilic acrylic.

Referring generally to FIGS. 20 - 26, in one embodiment the invention provides a variable optical strength intraocular lens complex 700 comprising an anterior lens segment 70 and a posterior lens segment 80. In one embodiment, the anterior lens segment 70 comprises a central optical zone 72 comprising a first 73 and a second 74 ciliary muscle haptics extending from a posterior surface of an anterior lens 77. In some embodiments, the first and second ciliary muscle haptics 73 each comprise two ciliary muscle plates 76 at a peripheral end. In some embodiments, the ciliary muscle plates 76 are each connected to a posterior surface of the anterior lens 77 by a ciliary haptic shaft 76. In some embodiments, pairs of ciliary haptic shafts 78 from adjacent ciliary muscle pates 76 are tethered via an adjustment band 79 for enabling adjustment of a relative length of each pair of ciliary haptic shafts 78. In some embodiments, the ciliary muscle plates 76 have a C-shaped cross-sectional area. In some embodiments, the ciliary muscle plates 76 having a C-shaped cross-sectional area comprise a first anterior segment 76A and a second posterior segment 76B having different lengths.

In one embodiment, the posterior lens segment 80 includes a haptic plate 81 and a posterior lens 88. The haptic plate 81 is sized to fit within the capsular bag 2 of the eye. In some embodiments, the haptic plate 81 includes at least one capsular bag haptic 11 which is shaped to secure the haptic plate 81 within the capsular bag 2 in a particular orientation with respect to the ciliary muscles 4. In some embodiments, the haptic plate 81 comprises 1 to a small plurality (i.e. 1 to about 4) of anchoring points 82 wherein the haptic plate 81 circumscribes a substantially circular central optical zone 83 having a perimeter, at least two circumferential springs 84 positioned on an anterior surface of the posterior lens segment 80 and at the perimeter of the central optical zone 83, and an anterior lens receptacle 85 adapted to receive the anterior lens 87, wherein the anterior lens receptacle 85 is in contact with the at least two circumferential springs 84. In one embodiment the anterior lens receptacle 85 has a curved edge of substantially the same radius of curvature as the anterior lens 87 and/or the substantially circular central optical zone 72.

A variable optical strength intraocular lens of this embodiment is placed substantially as described above. After removal of an existing lens or IOL is performed, the posterior lens segment is injected into the capsular bag. On unfolding, the anterior lens receptacle 85 on the posterior lens segment 80 extends through openings made in the capsular bag (capsulotomy) and is suspended in the sulcus. Next, the anterior lens segment is injected into the sulcus and unfolds as it passes through the anterior lens receptacle 85 on the posterior lens segment 80. The anterior lens 87 is fitted into the anterior lens receptacle 85 on the posterior lens segment 80. Finally, the first 74 and a second 74 ciliary muscle haptics are placed on ciliary muscle.

The present disclosure also includes use of the variable optical strength intraocular lens as described herein in any preceding paragraph alone or in combination to treat an eye disorder including but not limited to presbyopia and cataract.

2. Methods of Treating Eye Disorders

Variable optical strength IOLs of the present disclosure may be used to treat various eye disorders. Generally, a variable optical strength IOL 500 consistent with the present disclosure is implanted by a two-stage insertion method, with the lens complex 100 inserted first, followed by the ciliary haptic complex 400. In some embodiments, the lens complex 100 is folded before insertion into the eye (e.g., via an injector) to minimize the size of the required incision. In addition or in the alternative, the ciliary haptic complex 400 may be folded before insertion into the eye (e.g., via an injector) to minimize the size of the required incision.

Typically, removal of an existing lens or IOL is performed before insertion of the lens complex 400. For example, an existing lens may be phacoemulsified and removed using common surgical techniques. In the alternative, an IOL may be removed from the capsular bag 2 using common surgical techniques. The lens complex 400 may then be inserted into a loading cartridge using surgical micro-forceps. In some embodiments, the lens complex 400 is placed centrally in the loading cartridge over the central vertical fold of the cartridge with the posterior lens 9 in the most inferior position and the anterior lens 16 in a superior position to ensure correct unfolding within the capsular bag 2 and sulcus. Once securely in place, the cartridge is inserted into the injector and a gentle compression of the injector piston is given to ensure the lens complex 100 will vacate the injector successfully. In one embodiment, the injector nozzle is inserted via the corneal incision and guided to the empty capsular bag 2; once in position the lens complex 100 is inserted gradually into the capsular bag 2. As the lens complex 100 bypasses the injector nozzle it will partly unfold; at this point the unfolding lens complex is guided to the far end of the capsular bag 2 with compression of the injector piston to introduce more of the lens complex 100 into the capsular bag 2. On full unfolding the posterior lens 9 is surgically manipulated if needed to fit fully within the capsular bag 2. Once the haptic plate 10 is in contact with the inner surface of the capsular bag 2, the anterior lens 16 and spring(s) 13 will be centrally located within the capsular bag 2 and will protrude via the capsulotomy and settle suspended within the sulcus.

In one embodiment, with the lens complex 100 in place, the ciliary haptic complex 400 is loaded into a loading cartridge. In some embodiments, the ciliary haptic complex 400 is loaded into the injector after being folded along a folding zone of the central ring 17 defined by two discrete areas having a smaller diameter 18 than the remaining portions of the central ring 17. The nozzle of the injector is then placed into the corneal incision before ciliary haptic complex 400 is injected into the capsular bag 2. In some embodiments, the ciliary muscle plates 22 exit injector first; this enables initial positioning of one ciliary haptic 19 in engagement with ciliary muscles 4 at a desired location. The remainder of the ciliary haptic complex 400 is then injected into the capsular bag 2.

With the full ciliary haptic complex 400 inserted, the second ciliary haptic 19 is placed in engagement with ciliary muscle 4 at a second location, preferably substantially opposite the location of the first ciliary haptic 19. If needed, ciliary muscle plates 22 of one or both ciliary haptics 19 are placed in final position using surgical micro tools.

The lens complex 100 and the ciliary haptic complex 400 are then coupled to form the full functioning variable optical strength intraocular lens 500. Briefly, one end of the central ring 17 is guided to the inferior surface of the anterior lens 16. Then the opposite side of the central ring 17 is stretched over the opposing peripheral edge of the anterior lens 16. The central ring 17 is thus engaged on the inferior surface of the anterior lens 16 and superior to the spring(s) 13.

In one embodiment, after the lens complex 100 and the ciliary haptic complex 400 are coupled, the variable optical strength IOL 500 is calibrated. At the beginning of the procedure the patient's ciliary muscles are paralyzed and thus in their relaxed non contracted state. A microscope with wavefront aberrometer attachment or equivalent system may be used to obtain feedback readings (e.g., continuous feedback readings) from the eye. In one embodiment, based on the feedback readings, the adjustment band(s) 25 are moved along the ciliary haptic shafts 20 to alter the relative lengths of the ciliary haptics 19. In one embodiment, after each movement of the adjustment band(s) 25, another feedback reading is obtained. In one embodiment, this cycle is repeated until the feedback readings indicate that the variable optical strength IOL 500 does not provide an inappropriate myopic shift when the ciliary muscles 4 are in a relaxed state (i.e., when no accommodation is occurring).

After all calibrations are completed, the procedure concludes according to standard surgical methods commonly known to those of skill in the art.

In some embodiments, the present disclosure provides a method of treating a subject having an eye disorder, the method comprising removing a lens from the eye; inserting a lens complex 100 into the eye, the lens complex 100 comprising an anterior segment comprising an anterior lens 16, a posterior segment 8 comprising a posterior lens 9 and a haptic plate portion 10, wherein the haptic plate portion 10 substantially surrounds an optical zone Z, and at least one spring 13 in contact with the anterior segment and the posterior segment 8 to provide a separation distance between the anterior lens 16 and the posterior lens 9; inserting a ciliary haptic complex 400 into the eye, the ciliary haptic complex 400 comprising a central ring 17, a first ciliary muscle haptic 19 extending outwardly from the central ring 17, and a second ciliary muscle haptic 19 extending outwardly from the central ring 17; contacting ciliary muscle 4 of the eye with the first ciliary muscle haptic 19 and with the second ciliary muscle haptic 19; positioning the central ring 17 against an inferior side of the anterior lens 16 to form a variable optical strength intraocular lens 500; and calibrating the variable optical strength intraocular lens 500. In some embodiments, the step of positioning the central ring 17 comprises positioning a first portion of the central ring 17 against a first portion of the inferior side of the anterior lens 16; and sliding a second portion of the central ring 17 over the anterior lens 16 and against a second portion of the inferior side of the anterior lens 16. In some embodiments, the first and second ciliary muscle haptics 19 each comprise at least one ciliary muscle plate 22 at a peripheral end; a first ciliary muscle plate 22 connected to the central ring 17 by a first ciliary haptic shaft 20 and a second ciliary muscle plate 22 connected to the central ring 17 by a second ciliary haptic shaft 20; and an adjustment band 25 associated with each pair of first and second ciliary haptic shafts 20 for enabling adjustment of a relative length of each pair of first and second ciliary haptic shafts 20. In some embodiments, the step of calibrating the variable optical strength intraocular lens 500 comprises a) obtaining a wavefront aberrometer reading from the eye; b) sliding at least one of the adjustment bands 25 to adjust a length of at least one pair of the first and second ciliary haptic shafts 20; and c) repeating steps a) and b) if needed to avoid myopic shift when the ciliary muscle 4 is in a relaxed state. In some embodiments, the ciliary muscle 4 is in contact with the first ciliary muscle haptic 19 and with the second ciliary muscle haptic 19 at substantially opposing points of the ciliary muscle 4. In some embodiments, before the step of inserting the ciliary haptic complex 400 into the eye, the ciliary haptic complex 400 is folded across a fold plane of the central ring 17 defined by two discrete areas 18 having a smaller diameter than a diameter of the remainder of the central ring 17. In some embodiments, the two discrete areas 18 having a smaller diameter are located at substantially opposing regions of the central ring 17. In some embodiments, after insertion of the folded ciliary haptic complex 400 into the eye, the ciliary haptic complex 400 is unfolded. In some embodiments, the two discrete areas 18 having a smaller diameter are offset from first and second attachment zones 21, wherein the first attachment zone 21 is defined by a junction between the first ciliary haptic shaft 20 and the central ring 17 and the second attachment zone 21 is defined by a junction between the second ciliary haptic shaft 20 and the central ring 17. In some embodiments, the step of contacting the ciliary muscle 4 with the first ciliary muscle haptic 19 and with the second ciliary muscle haptic 19 comprises contacting a first location of the ciliary muscle 4 with at least one ciliary muscle plate 22 positioned at a peripheral end of the first ciliary muscle haptic 19; and thereafter contacting a second location of the ciliary muscle 4 with at least one ciliary muscle plate 22 positioned at a peripheral end of the second ciliary muscle haptic 19, wherein the first location of the ciliary muscle 4 is substantially opposite from the second location of the ciliary muscle 4. In some embodiments, the method further comprises folding the lens complex 100 before the step of inserting the lens complex 100 into the eye; and unfolding the lens complex 100 after the step of inserting the lens complex 100 into the eye. In some embodiments, the eye disorder is presbyopia. In some embodiments, the eye disorder is a cataract.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:
1. A variable optical strength intraocular lens comprising:
   a lens complex comprising:
      an anterior segment comprising an anterior lens,
      a posterior segment comprising a posterior lens portion and a haptic plate portion, wherein the haptic plate portion surrounds an optical zone, and
      at least one spring in contact with the anterior segment and the posterior segment to provide a separation distance between the anterior lens and the posterior lens portion, and
      at least one spring comprises one, two, three, four, or more than four springs having a C-shaped cross-section; and
   a ciliary haptic complex comprising:
      a central ring,
      a first pair of ciliary muscle haptics extending outwardly from the central ring, and
      a second pair of ciliary muscle haptics extending outwardly from the central ring wherein upon insertion into an eye, the central ring is in contact with an inferior side of the anterior lens and the first pair of ciliary muscle haptics and the second pair of ciliary muscle haptics are in communication with ciliary muscle of the eye and wherein contraction of the ciliary muscle causes the separation distance between the anterior lens and the posterior lens to increase.

2. The variable optical strength intraocular lens of claim 1, wherein a posterior surface of the posterior segment comprises:
   the haptic plate portion comprises a drainage slit,
   a continuous inner squared edge surrounding the optical zone,
   an interrupted outer squared edge surrounding the continuous inner squared edge, and
   an inter-squared edge channel between the continuous inner squared edge and the interrupted outer squared edge for accommodating aqueous fluid upon insertion into an eye wherein the inter-squared edge channel is in fluid communication with the drainage slit.

3. The variable optical strength intraocular lens of claim 1, wherein the ciliary haptics comprises:
   the first pair and the second pair of ciliary muscle haptics each comprise two ciliary muscle plates at a peripheral end,
   the first pair of ciliary muscle haptics and the second pair of ciliary muscle haptics each comprise a first ciliary muscle plate connected to the central ring by a first ciliary haptic shaft and a second ciliary muscle plate connected to the central ring by a second ciliary haptic shaft,
   each pair of first and second ciliary haptic shafts further includes an adjustment band that is slidably associated with at least one of the ciliary hepatic shafts,
   at least one ciliary muscle plate has a curved C-shaped cross-sectional area comprises a first anterior segment and a second posterior segment,
   wherein the second posterior segment is longer than the first anterior segment, a junction between the first ciliary haptic shaft and the central ring and a junction between the second ciliary haptic shaft and the central ring define attachment zones, and wherein the two discrete areas of secondary thickness are adjacent to the attachment zones, the central ring comprises two discrete areas of primary thickness and two discrete areas of secondary thickness, wherein the two discrete areas of secondary thickness have a smaller diameter than the two discrete areas of primary thickness and are located at opposing regions of the central ring to define a folding zone.

4. The variable optical strength intraocular lens of claim 1, wherein the haptic plate portion further comprises at least one capsular bag haptic at a peripheral edge.

5. The variable optical strength intraocular lens of claim 1, wherein the lens complex is formed of a material selected from the group consisting of: a hydrophobic acrylic, a hydrophilic acrylic, a silicone, and combinations thereof.

6. The variable optical strength intraocular lens of claim 1, wherein the ciliary haptic complex is formed of a material selected from the group consisting of: a hydrophobic acrylic, a hydrophilic acrylic, a silicone, and combinations thereof.

7. A variable optical strength intraocular lens complex comprising,
an anterior lens segment comprising an anterior lens and a first and second ciliary muscle haptic extending from a posterior surface of the anterior lens; and
a posterior segment comprising a posterior lens segment comprising a haptic plate and a posterior lens wherein the haptic plate substantially surrounds an optical zone having a perimeter, at least two circumferential springs positioned on an anterior surface of the posterior lens segment at the perimeter of the optical zone, and an anterior lens receptacle adapted to receive the anterior lens, wherein the anterior lens receptacle is in contact with the at least two circumferential springs.

8. The variable optical strength intraocular lens complex of claim 7 wherein the anterior lens receptacle has a curved edge of substantially the same radius of curvature as the anterior lens and/or the optical zone.

9. The variable optical strength intraocular lens complex of claim 8 wherein the haptic plate comprises a plurality of anchoring points.

10. A variable optical strength intraocular lens comprising:
a lens complex comprising:
an anterior segment comprising an anterior lens,
a posterior segment comprising a posterior lens portion and a haptic plate portion, wherein the haptic plate portion surrounds an optical zone, and
at least one spring in contact with the anterior segment and the posterior segment to provide a separation distance between the anterior lens and the posterior lens portion, and
at least one spring comprises one, two, three, four, or more than four springs having a C-shaped cross-section; and
a ciliary haptic complex comprising:
a central ring,
a first pair of ciliary muscle haptics extending outwardly from the central ring, and
a second pair of ciliary muscle haptics extending outwardly from the central ring wherein upon insertion into an eye, the central ring is in contact with an inferior side of the anterior lens and the first pair of ciliary muscle haptics and the second pair of ciliary muscle haptics are in communication with ciliary muscle of the eye and wherein contraction of the ciliary muscle causes the separation distance between the anterior lens and the posterior lens to increase;
the first pair and the second pair of ciliary muscle haptics each comprise two ciliary muscle plates at a peripheral end,
the first pair of ciliary muscle haptics and the second pair of ciliary muscle haptics each comprise a first ciliary muscle plate connected to the central ring by a first ciliary haptic shaft and a second ciliary muscle plate connected to the central ring by a second ciliary haptic shaft,
each pair of first and second ciliary haptic shafts further includes an adjustment band that is slidably associated with at least one of the ciliary hepatic shafts,
at least one ciliary muscle plate has a curved C-shaped cross-sectional area comprises a first anterior segment and a second posterior segment, wherein the second posterior segment is longer than the first anterior segment,
a junction between the first ciliary haptic shaft and the central ring and a junction between the second ciliary haptic shaft and the central ring define attachment zones, and wherein the two discrete areas of secondary thickness are adjacent to the attachment zones,
the central ring comprises two discrete areas of primary thickness and two discrete areas of secondary thickness, wherein the two discrete areas of secondary thickness have a smaller diameter than the two discrete areas of primary thickness and are located at opposing regions of the central ring to define a folding zone.

* * * * *